US009215985B2

United States Patent
Gross et al.

(10) Patent No.: US 9,215,985 B2
(45) Date of Patent: Dec. 22, 2015

(54) METHOD AND APPARATUS FOR MONITORING A TREATMENT OF A PATIENT, PREFERABLY FOR MONITORING HEMODIALYSIS, HEMODIAFILTRATION, AND/OR PERITONEAL DIALYSIS

(75) Inventors: Malte Gross, Ulm (DE); Pascal Kopperschmidt, Dittelbrunn (DE); Andreas Maierhofer, Schweinfurt (DE); Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 14/111,248

(22) PCT Filed: Apr. 10, 2012

(86) PCT No.: PCT/EP2012/056472
§ 371 (c)(1),
(2), (4) Date: Nov. 20, 2013

(87) PCT Pub. No.: WO2012/140022
PCT Pub. Date: Oct. 18, 2012

(65) Prior Publication Data
US 2014/0098359 A1    Apr. 10, 2014

Related U.S. Application Data

(60) Provisional application No. 61/473,850, filed on Apr. 11, 2011.

(30) Foreign Application Priority Data

Apr. 11, 2011  (EP) .................................. 11161916

(51) Int. Cl.
G01N 21/00   (2006.01)
A61B 5/00    (2006.01)
(Continued)

(52) U.S. Cl.
CPC ............. *A61B 5/0082* (2013.01); *A61B 5/0071* (2013.01); *A61B 5/0075* (2013.01); *A61B 5/14546* (2013.01); *A61B 5/14557* (2013.01); *A61M 1/367* (2013.01); *G01N 21/6486* (2013.01); *G01N 21/65* (2013.01)

(58) Field of Classification Search
CPC ... H01J 37/32935; G01N 21/64; G01N 21/68; G01N 2015/1037; G01J 3/02
USPC ............................................. 356/301, 72–73
See application file for complete search history.

(56) References Cited

U.S. PATENT DOCUMENTS 7,674,236 B2   3/2010  Daniel et al.
8,269,953 B2   9/2012  Bado et al.
(Continued)

FOREIGN PATENT DOCUMENTS

CN    101098721    1/2008
CN    101479595    7/2009
(Continued)

*Primary Examiner* — Abdullahi Nur
(74) *Attorney, Agent, or Firm* — Jacobson Holman, PLLC.

(57) ABSTRACT

A method of monitoring a treatment of a patient, preferably for monitoring hemodialysis, hemodiafiltration and/or peritoneal dialysis, that includes the steps of irradiating a sample of a dialysis liquid used in the treatment with irradiation light of at least a first irradiation wavelength, detecting light emitted by the irradiated sample in at least a first detection wavelength, the detection wavelength being different from the first irradiation wavelength, and determining the presence and/or concentration of at least one analyte in the sample on the basis of the detected light.

24 Claims, 4 Drawing Sheets

(51) Int. Cl.
 *A61M 1/36* (2006.01)
 *A61B 5/145* (2006.01)
 *A61B 5/1455* (2006.01)
 *G01N 21/64* (2006.01)
 *G01N 21/65* (2006.01)

(56) References Cited

U.S. PATENT DOCUMENTS

2004/0204634 A1 10/2004 Womble et al.
2007/0109535 A1* 5/2007 Maier et al. .................. 356/301
2008/0158544 A1 7/2008 Womble et al.
2013/0153474 A1 6/2013 Frorip et al.

FOREIGN PATENT DOCUMENTS

| | | |
|---|---|---|
| CN | 102946919 | 2/2013 |
| DE | 102008027085 | 5/2010 |
| EP | 0575712 | 12/1993 |
| JP | 2004061314 | 2/2004 |
| WO | WO 2008/136548 | 11/2008 |
| WO | WO 2010/091826 | 8/2010 |

* cited by examiner

METHOD AND APPARATUS FOR MONITORING A TREATMENT OF A PATIENT, PREFERABLY FOR MONITORING HEMODIALYSIS, HEMODIAFILTRATION, AND/OR PERITONEAL DIALYSIS

CROSS-REFERENCE TO RELATED APPLICATION

This is a national stage of PCT/EP12/056472 filed Apr. 10, 2012 and published in English, which has a priority of Europe no. 11161916.9 filed Apr. 11, 2011, U.S. provisional application No. 61/473,850, filed Apr. 11, 2011, hereby incorporated by reference.

BACKGROUND OF THE INVENTION

1. Field of Invention

The present invention pertains to a method and an apparatus for monitoring a treatment of a patient, preferably for monitoring hemodialysis, hemodiafiltration and/or peritoneal dialysis.

2. Description of the Prior Art

Extracorporeal treatment methods have been used for a long time for treating different conditions. Dialysis is the most commonly known and used extracorporeal treatment method which is intended to replace the function of the kidneys when a renal failure of the kidneys occurred in a patient.

When the kidneys fail, dialyzing a patient is necessary to remove waste products such as urea, creatinine and uremic toxins from the blood of the patient. Furthermore, during dialysis, excess water and other substances which are usually eliminated by urine are removed from the body of the patient. The most commonly used method of dialysis is hemodialysis in which the blood of the patient flows along a dialyzing membrane, wherein on the other side of this dialyzing membrane a dialyzing liquid is provided. Accordingly, blood and dialyzing liquid are separated by the porous membrane.

Through this membrane, the substances which are to be removed from the blood of the patient diffuse because of a concentration gradient between blood and the dialyzing liquid. Larger molecules, whose diffusion velocity is very slow, can also be transported convectively by means of a liquid flow from the blood side to the dialysis liquid side of the membrane.

The dialysis liquid is prepared to have a concentration which provides for a concentration gradient from the blood side to the dialysis liquid side for certain substances, but not necessarily for all substances. In fact, the removal of urea and creatinine as well as other waste products in the human body is desired but, for example, the removal or change of concentration of electrolytes such as potassium, sodium or bicarbonate is not at all desired but is considered harmful. Accordingly, the dialysis liquid typically contains a concentration of the electrolytes which resembles the concentration of electrolytes in the blood plasma of the patient such that a concentration gradient is not present for these substances.

Besides the hemodialysis, peritoneal dialysis is another dialysis method which also uses a membrane and a dialysis liquid in order to achieve a diffusion of the waste product through the membrane into the dialysis liquid. The membrane, however, is a natural membrane namely the peritoneum and the dialysis liquid is introduced directly into the abdominal cavity.

During dialysis, the elimination of excess water and small molecular uremic substances such as urea and creatinine is typically no problem, larger molecules, however, are more difficult to remove through the porous membrane. In order to tackle this, specific high flux dialysis membranes are provided in combination with highly convective methods, such as hemodiafiltration. This results in improvements in the clearance of molecules of molecular masses over 1 kDa, which is the range of the so-called middle-sized molecules. In hemodiafiltration, a diffusion method using the dialysis liquid in the form as described above is combined with hemofiltration, in which the blood of a patient is subjected to a pressure gradient across a filter. Accordingly, the filtration process along the pressure gradient leads to an increased liquid flow and is, thus, considered a highly convective method which enables the removal of a considerable portion of middle-sized molecules. However, due to the pressure gradient, water as well as electrolytes and sugars are also removed from the blood of the patient at a high rate such that these blood constituents have to be replaced by means of the infusion of a replacement fluid.

The introduction of the high flux dialysis membranes in combination with highly convective methods improves the clearance for middle-sized and larger molecules.

Larger molecules are typically proteins, wherein, for example, beta2-microglobulin has a size of about 11 kDa, wherein this molecule may induce an amyloidosis if not sufficiently removed. Smaller molecules which are toxic may also be difficult to dialyze if the molecules are bound to proteins. For example, uremic toxins which are bound to proteins are p-cresyl sulfate and indoxyl sulfate.

Accordingly, it is desired to have pore sizes in the dialysis membranes which are sufficiently large to let through these middle-sized molecules. On the other hand, the pore size of the membrane cannot be extended infinitely, because the higher the pore size of the membrane, the higher the risk that vital blood components are likewise lost. Accordingly, the permeability of the membrane is typically limited to sizes of around 60 kDa. However, this value is just slightly below the molecular mass of human plasma albumin which has a size of about 66 kDa. In practice, clinically significant losses of albumin may happen wherein these losses significantly depend on the respective parameters of the method, such as the respective pressures and the respective concentrations in the dialysis liquid. In particular, a high flux membrane in combination with the pressure gradient applied during hemofiltration increases the clearance of human albumin. Another reason for the loss of human albumin may be the multiple use of the membranes because the cleaning of the membrane which is necessary between different treatments tends to increase the sizes of the pores in the membrane. This shifts the permeability of the membrane towards higher molecules. Accordingly, even under normal conditions in normal hemodialysis, human serum albumin may penetrate through the membrane.

It goes without saying that in the case of the peritoneal dialysis the sizes of the pores of the membrane cannot be influenced but are given by the condition of the peritoneum of the respective patient. However, a loss of human albumin into the dialysis liquid may nevertheless take place once the peritoneum has been impaired, for example, by an inflammation.

In order to determine the clearance of an analyte during dialysis, a Raman spectroscopy method is disclosed in US 2008/0158544 A1, wherein the Raman spectral measurements are carried out on the blood after it has passed the dialyzer in order to utilize the unique Raman spectroscopic signature of one or more analytes, e.g., urea, to identify and quantify such analytes against a whole blood background.

WO 2010/091826 A1 relates to an apparatus for the extracorporeal treatment of blood, wherein the absorption of electromagnetic radiation in the dialysis liquid is measured in order to determine the Kt/V value, namely the clearance K of the volume flow of the clean substances, wherein t is the treatment time and V the distribution volume of the patient. In renal replacement therapy, urea is typically used as a marker substance for measuring treatment efficiencyuric acid, such that K is the uric acid clearance and V the urea distribution volume of the patient, which corresponds, in principle, to the body water of the patient. However, by measuring the total absorption, in general the clearance for a specific molecule cannot be determined.

SUMMARY OF THE INVENTION

Accordingly, it is an object of the present invention to provide a method and an apparatus for monitoring a treatment of a patient.

According to the present invention, a method for monitoring a treatment of a patient, preferably for monitoring hemodialysis, hemodiafiltration and/or peritoneal dialysis, is suggested. The method comprises the steps of irradiating a sample of a dialysis liquid used in the treatment with irradiation light of at least a first irradiation wavelength, detecting light emitted by the irradiated sample in at least a first detection wavelength, the detection wavelength being different from the first irradiation wavelength, and determining the presence and/or concentration of at least one analyte in the sample on the basis of the detected emission light.

By means of the irradiation of the sample of dialysis liquid with light of at least a first irradiation wavelength and the detection of light of at least a first detection wavelength, wherein the detection wavelength is different from the first irradiation wavelength, it becomes possible to determine the emission response of an analyte in the dialysis liquid. The presence and/or concentration of specific analytes, such as human albumin, can be monitored in the dialysis liquid in order to monitor the treatment of the patient. In case, for example, that the concentration of the human albumin in the dialysis liquid exceeds a predetermined concentration, an alarm might be released and the replacement of the dialysis membrane might be required. On the other hand, the concentration of uremic toxins such as beta2-microglobulin can be used to monitor and optimize the treatment efficiency by adjusting the treatment modalities.

Preferably, the detected light includes fluorescence light and the presence and/or concentration of the at least one analyte in the sample is determined on the basis of the detected fluorescence light.

To illustrate this, in fluorescence spectroscopy, a sample is irradiated with irradiation light of a predetermined wavelength. The light beam of the irradiation light, usually ultraviolet light, excites the electrons of certain analytes to a higher energy level. By the absorption of a photon, the molecule is excited from its ground electronic state to one of the various vibrational states in the excited electronic state. When, after a short time, the molecule relaxes again into the ground electronic state, a photon is emitted. Because a portion of the energy is dissipated by means of non-radiating transitions, for example collisions with other molecules which cause the excited molecule to loose vibrational energy, the photon emitted in the process has a lower energy and, thus, a longer wavelength than the exciting photon. Accordingly, the irradiation wavelength of the light exciting the molecule is different from the detection wavelength of the emitted photon such that the irradiation light and the emitted light can be easily distinguished spectroscopically.

Because the excitation wavelength as well as the emission wavelength can be chosen relatively freely in comparison to absorption spectroscopy, more detailed information on the analytes dissolved in the dialysis liquid can be obtained by means of the method. Furthermore, as the intensity of the detected light is typically proportional to the concentration of the analyte or, specifically, of the fluorophore in the dialysis liquid, the intensity of the detected light may serve as a measure for the actual concentration of the respective analyte in the dialysis liquid.

In a preferred embodiment, the detection wavelength is different from each of the irradiation wavelengths. This has the advantage that the setup for detecting the light can be simplified because the detection is always carried out at wavelengths different from the irradiation such that the irradiation light can be blocked from entering the detector by means of devices known in the art.

For example, the fluorescence intensity is proportional to the product of the absorption coefficient E at the excitation wavelength and the quantum yield $\phi_F$. The latter refers to the ratio of the absorbed photons to the number of photons emitted by means of fluorescence.

By means of the determination of the presence and/or concentration of at least one analyte in the sample on the basis of the detected light, for example on the basis of the fluorescence of the respective analyte, the presence and/or concentration of specific molecules can be determined. It is advantageous vis-à-vis the conventional absorption measurement that only a small number of molecules which are present in the dialysis liquid are active with respect to light emission, for example fluorescence. In particular, the substances such as uric acid, which are present in the dialysis liquid in very high concentrations, do not show any fluorescence and do not disturb, therefore, the measurement of the specific molecules. Proteins and the above mentioned uremic toxins, however, can be determined by means of a fluorescence measurement particularly well.

In comparison with absorption spectroscopy, fluorescence spectroscopy is much more sensitive. In fact, when comparing the present method to absorption spectroscopy where very low concentrations of certain components lead only to minor absorption and thus to very small attenuation of the light sent through the sample, the present method has the advantage that the intensity of the fluorescence light is directly proportional to the concentration of the respective analyte in the sample such that the sensitivity of a sensor/detector can be used in an optimum manner.

Exemplary groups of proteins which are fluorescence active are the aromatic side chains of the amino acids phenylalanine, tyrosine and tryptophan.

When considering the fluorescence activity of these amino acids, tyrosine and tryptophan dominate the fluorescence of the proteins. With a sufficiently long excitation wavelength, namely an excitation wavelength of $\lambda_{ex} \geq 295$ nm, tryptophan is the only amino acid which is fluorescence active. Even though tryptophan is an amino acid which is relatively rare, the albumin molecule includes one tryptophan unit. Due to the high fluorescence efficiency of tryptophan, albumin can thus be detected with sufficient efficiency.

In order to increase the accuracy of the method, the detection light is preferably detected in at least a first detection wavelength and a second detection wavelength, the first and second detection wavelengths being different from one another. Preferably, the detection light is detected by detecting a portion or the entire spectrum of the emitted light of the sample. By detecting more than one wavelength of the emitted light, the correlation of the detection light and a corresponding emission fingerprint, in particular a fluorescence fingerprint, of a specific analyte becomes even more accurate. The emission spectrum for a specific irradiation wavelength can be compared with specific emission fingerprints of the analytes which are relevant, in particular with the emission fingerprints of specific molecules of interest which are intended to be monitored in the extracorporeal treatment method. In fact, it is interesting to monitor, in the dialysis liquid, the presence and/or concentration of free fluorescent amino acids, of albumin, of indoxyl sulfate and of any other fluorescent uremic toxins in order to determine the clearance for the respective molecules.

As an alternative or as a supplement to the analysis of fluorescence light, Raman scattered light may be used for the determination of the presence and/or concentration of a certain analyte in the sample. To this end, the Raman emission of the sample is measured either over the whole Raman spectrum, over a portion thereof or over certain detection wavelengths and the respective intensities or spectra are compared to Raman fingerprints of the respective analytes of interest.

In order to further increase the accuracy of the determination of the presence and/or concentration of the analyte, the sample is preferably irradiated by an irradiation light in the UV-range, preferably with irradiation light having a wavelength of between 180 nm and 400 nm, more preferably at 250 nm to 300 nm, most preferred at 280 nm and/or 295 nm. Preferably, the sample is irradiated with irradiation light of at least two separated, distinct irradiation wavelengths, preferably at 280 nm and 295 nm. The two different emission spectra induced by the two irradiation wavelengths may be compared and the efficiency and accuracy of the determination of the analyte be even more increased.

In order to compensate for absorption of the irradiation light in the sample, the intensity of the irradiation light in the sample is preferably determined and the determination of the presence and/or concentration of the analyte in the sample is compensated for the intensity of the irradiation light. Preferably the absorption of the irradiation light in the sample is measured and the intensity of the irradiation light is determined on the basis of the measured absorption, wherein preferably the absorption in the sample is measured by means of a photo detector detecting the irradiation light transmitted through the sample.

Alternatively, the intensity of Raman scattered light of the sample is measured and is used to determine the intensity of the irradiation light. This measurement of the Raman scattered light may be carried out at the intensity peak of the Raman scattered light in water.

The step of compensating for the absorption of light in the sample takes care of the fact that the dialysis liquid may have a different absorption, depending on the efficiency of the dialysis process as well as on the basis of the different conditions of the respective patient. In fact, at the beginning of a dialysis session, the dialysis liquid may contain a significantly higher proportion of uric acid, creatinine and other waste products which have a high absorption for the excitation light than in a later status of the dialysis process. In order to be in a position to safely determine the presence and/or concentration of the respective analyte in the sample, it is important to determine the respective absorption of the sample such that it is clear what is the actual excitation intensity which results in the respective fluorescence spectrum and the respective fluorescence intensity.

Even further information on the presence and/or concentration of an analyte in the sample can be obtained when preferably detecting the fluorescence light in a time resolved manner, preferably wherein the irradiation light is pulsed.

Other forms of analysis of the analytes may be present by irradiating the sample with polarized light, preferably with left-handed circularly polarized light and/or right-handed circularly polarized light.

In order to further improve the method, the fluorescence light of the sample is preferably detected at least twice, wherein between the first and second detections the sample is treated physically and/or chemically and the presence and/or concentration of the analyte is determined taking into account the difference between the first and second detections, wherein the sample is preferably treated by heating, by adding and/or removing of reagents and/or by adding and/or removing of an acid, of a chemical base and/or of a salt.

To be in a position to carry out more complex measurements, the sample may be separated from the flow of dialysis liquid for carrying out the determination of the presence and/or concentration of the analyte.

In an alternative, the determination of the presence and/or concentration of the analyte may be carried out continuously on the flow of dialysis liquid.

In yet another preferred version, before irradiating the sample with the irradiation light, the sample is separated into different fractions, preferably by means of ultrafiltration, electrophoresis, chromatography, the addition of absorber and/or the addition of a fluorescent marker, and at least one of the fractions of the sample is irradiated with the irradiation light.

When monitoring the analyte in the dialysis liquid, in particular when monitoring the presence and/or absence of albumin, it can be seen that human albumin emits a fluorescent light which has a maximum at 340 nm when it is excited at about 280 nm.

Indoxyl sulfate (indican) which is a waste product of tryptophan, is known to be present in uremic patients in a significant concentration in the blood serum. Indoxyl sulfate is known to be a uremic toxin. The fluorescence spectra of tryptophan and indoxyl sulfate are considerably similar such that, besides the proteins of the dialysis, the clearance of indoxyl sulfate is interesting in diagnostic aspects. As an alternative, fluorescence markers binding to certain molecules may be used to determine the presence and/or concentration of the respective molecules.

In order to even more precisely determine the composition of the used dialysis liquid, the presence and/or concentration of at least two different analytes may be determined on the basis of the detected light.

Preferably, after excitation with a specific wavelength by irradiation of the sample with the irradiation light, the detected light may be analysed as to the presence of the at least N different analytes. This is done by analyzing the detected spectrum $f(\lambda)$, i.e. the intensities at the respective emission wavelength $\lambda$, which is assumed to be given in the form of a linear superposition of the emission spectra of the N analytes:

$$f(\lambda) = \sum_{i=1}^{N} c_i s_i(\lambda)$$

$c_i$ being the unknown concentration of the $i^{th}$ analyte and $s_i(\lambda)$ being the known emission sensitivity of the $i^{th}$ analyte as a function of the respective emission wavelength $\lambda$. This equation is preferably solved for the unknown concentrations $c_i$ by determining the spectrum at M different discrete emission wavelengths $\lambda_j$, considering the above equation in the form of the following system of M equations with N unknowns:

$$\begin{pmatrix} f(\lambda_1) \\ f(\lambda_2) \\ \vdots \\ f(\lambda_M) \end{pmatrix} = \begin{pmatrix} s_1(\lambda_1) & s_2(\lambda_1) & \ldots & s_N(\lambda_1) \\ s_1(\lambda_2) & s_2(\lambda_2) & \ldots & s_N(\lambda_2) \\ \vdots & \vdots & \ddots & \vdots \\ s_1(\lambda_M) & s_2(\lambda_M) & \ldots & s_N(\lambda_M) \end{pmatrix} \begin{pmatrix} c_1 \\ c_2 \\ \vdots \\ c_N \end{pmatrix}$$

This system is solved numerically, preferably by considering as the best solution for the above system of equations the one which provides, when being inserted into the above matrix, the superposition spectrum which has the lowest square deviation from the actually measured spectrum. By means of this analysis it becomes possible determining the composition of the dialysis fluid by analyzing the detected emission light and in particular by analyzing the respective spectrum of the detected emission light. In particular, the unknown concentrations $c_i$ are determined and, thus, the composition of the used dialysis fluid with respect to the concentrations $c_i$ of the respective analytes can be determined.

This method can be extended to more than one, namely P, irradiation wavelengths $\lambda_{irr}$, P being larger than one, when for each irradiation wavelength $\lambda_{irr}$ a separate emission spectrum $f(\lambda_{irr},\lambda)$ is detected at the respective emission wavelength $\lambda$. Accordingly, the detected spectrum $f(\lambda_{irr},\lambda)$ for one irradiation wavelength $\lambda_{irr}$ is assumed, again, to be given in the form of a linear superposition of the emission spectra of the N analytes:

$$f(\lambda_{irr}, \lambda) = \sum_{i=1}^{N} c_i s_i(\lambda_{irr}, \lambda)$$

$c_i$ being the unknown concentration of the $i^{th}$ analyte and $s_i(\lambda_{irr},\lambda)$ being the known emission sensitivity of the $i^{th}$ analyte as a function of the emission wavelength $\lambda$ at the respective irradiation wavelength $\lambda_{irr}$.

By adding the respective equations to the linear equation system given above, it reads:

$$\begin{pmatrix} f(\lambda_{irr1}, \lambda_1) \\ f(\lambda_{irr1}, \lambda_2) \\ \vdots \\ f(\lambda_{irr1}, \lambda_M) \\ f(\lambda_{irr2}, \lambda_1) \\ f(\lambda_{irr2}, \lambda_2) \\ \vdots \\ f(\lambda_{irr2}, \lambda_M) \\ \vdots \\ f(\lambda_{irrP}, \lambda_1) \\ \vdots \\ f(\lambda_{irrP}, \lambda_M) \end{pmatrix} = \begin{pmatrix} s_1(\lambda_{irr1}, \lambda_1) & s_2(\lambda_{irr1}, \lambda_1) & \ldots & s_N(\lambda_{irr1}, \lambda_1) \\ s_1(\lambda_{irr1}, \lambda_2) & s_2(\lambda_{irr1}, \lambda_2) & \ldots & s_N(\lambda_{irr1}, \lambda_2) \\ \vdots & \vdots & \ldots & \vdots \\ s_1(\lambda_{irr1}, \lambda_M) & s_2(\lambda_{irr1}, \lambda_M) & \ldots & s_N(\lambda_{irr1}, \lambda_M) \\ s_1(\lambda_{irr2}, \lambda_1) & s_2(\lambda_{irr2}, \lambda_1) & \ldots & s_N(\lambda_{irr2}, \lambda_1) \\ s_1(\lambda_{irr2}, \lambda_2) & s_2(\lambda_{irr2}, \lambda_2) & \ldots & s_N(\lambda_{irr2}, \lambda_2) \\ \vdots & \vdots & \ldots & \vdots \\ s_1(\lambda_{irr2}, \lambda_M) & s_2(\lambda_{irr2}, \lambda_M) & \ldots & s_N(\lambda_{irr2}, \lambda_M) \\ \vdots & \vdots & \ldots & \vdots \\ s_1(\lambda_{irrP}, \lambda_1) & s_2(\lambda_{irrP}, \lambda_1) & \ldots & s_N(\lambda_{irrP}, \lambda_1) \\ \vdots & \vdots & \ldots & \vdots \\ s_1(\lambda_{irrP}, \lambda_M) & s_2(\lambda_{irrP}, \lambda_M) & \ldots & s_N(\lambda_{irrP}, \lambda_M) \end{pmatrix} \begin{pmatrix} c_1 \\ c_2 \\ \vdots \\ \\ \\ \\ \\ \\ \\ \\ \\ c_N \end{pmatrix}$$

By solving the above equation system, preferably in the same fashion as indicated above, a solution for the concentrations $c_i$ can be determined and, thus, the concentrations of the respective analytes in the used dialysis liquid can be determined.

The objective given above is also solved by means of an apparatus for monitoring a treatment of a patient, preferably for monitoring hemodialysis, hemodiafiltration and/or peritoneal dialysis with the features described herein.

Accordingly, the apparatus for monitoring a treatment of a patient, preferably for monitoring hemodialysis, hemodiafiltration and/or peritoneal dialysis, the apparatus comprises a light source for irradiating a sample of a dialysis liquid used in the treatment with irradiation light of at least a first irradiation wavelength, a detector for detecting light emitted by the irradiated sample in at least a first detection wavelength, the detection wavelength being different from each irradiation wavelength, and a control and analysis unit for determining the presence and/or concentration of at least one analyte in the sample on the basis of the detected light.

Further preferred embodiments of the apparatus are as described herein.

BRIEF DESCRIPTION OF THE DRAWINGS

The present disclosure will be more readily appreciated by reference to the following detailed description when being considered in connection with the accompanying drawings in which.

DETAILED DESCRIPTION OF THE PREFERRED EMBODIMENTS

Figure 1:
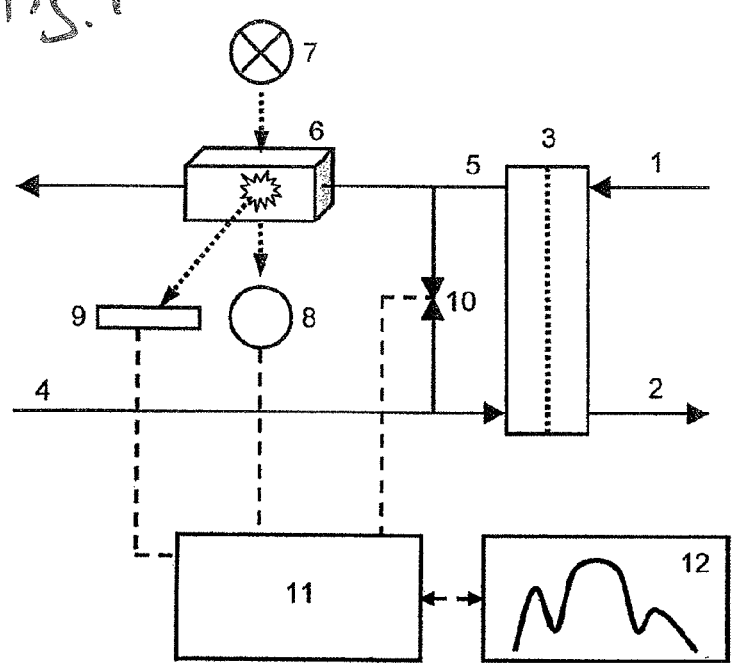
FIG. 1 is a schematic view of an apparatus for monitoring an analyte in an extracorporeal treatment.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the following, the disclosure will be explained in more detail with reference to the accompanying Figures. In the Figures, like elements are denoted by identical reference numerals and repeated description thereof may be omitted in order to avoid redundancies.

FIG. 1 is a schematic view of a system for treating a patient, in particular an apparatus for dialysis. The system includes an apparatus for monitoring the treatment of a patient.

In particular, FIG. 1 shows a dialyzer comprising a porous, semi-permeable membrane 3. On the right-hand side of FIG. 1 the blood circulation of the patient is connected to the membrane 3 and on the left-hand side the dialyzing liquid circulation is connected to the membrane 3. The principle of hemodialysis is well known and involves the diffusion of solutes in the blood through the semi-permeable membrane 3. The diffusion is induced by a concentration gradient of certain substances across the membrane 3.

Blood from the patient is transported via conduit 1 to the membrane 3 and passes along the membrane on one side of it towards conduit 2, from which the blood is transported back to the patient.

The dialyzing liquid is transported via conduit 4 to the membrane 3 and is discarded via conduit 5. From FIG. 1, it becomes immediately apparent that, in this specific embodiment, the blood circulation and the dialyzing liquid circulation involve opposing fluid streams on the membrane 3. The method utilizes counter current flows such that fresh dialyzing liquid comes in contact with the blood of the patient that is going to be transported back to the patient again and fresh blood from the patient comes in contact with the dialyzing liquid that is about to be discarded. This is standard practice to increase the efficiency of the dialyzing process because the counter current flow maintains the concentration gradient across the membrane at a maximum and increases the efficiency of the dialysis. However, in alternative solutions a parallel flow of blood and dialysis fluid may also be used, depending on the therapeutic needs of the patient.

The membrane 3 is a porous, semi-permeable membrane as is customary when in dialysis apparatus. Due to the concentration gradient between the patient side and the dialysis liquid side of the membrane 3, molecules diffuse from the blood side through the semi-permeable membrane 3 to the dialysis liquid side and are, such, removed from the blood.

Depending on the actual conditions of the patient and depending on the effect that is intended to be achieved, the dialysis liquid includes concentrations of different substances which are intended to match the concentrations in the blood, such that a concentration gradient is not present. This may be the case, for example, for electrolytes which consequently do not diffuse through the membrane 3. However, other substances may not at all be present in the fresh dialysis liquid such that a strong concentration gradient is induced. This strong concentration gradient is desired, in particular, for substances which are normally eliminated via urine such as uric acid, creatinine and the uremic toxins. Excess water in the blood is also intended to be removed. Depending on the sizes of the pores of the membrane 3, however, diffusion of larger molecules such as, for example, human albumin might also occur. This is, however, not desired.

A sample of the used dialysis liquid, which is discharged via the conduit 5, is analyzed in a cell 6 with respect to the presence and/or concentration of at least one analyte. To this end, a light source 7 is present which irradiates the sample of dialysis liquid present in the cell 6 with an excitation light. The light source 7 preferably emits at least one first wavelength, preferably a wavelength of light in the ultraviolet range, namely in a range between 180 nm and 400 nm. In the specific embodiment shown in FIG. 1, the light source 7 is a semi-conductor based light source for the ultraviolet range, in particular an AlInGaN-diode emitting light at a wavelength of 280 nm. However, any other suitable light source may be used.

The sample of dialysis liquid present in cell 6 is illuminated by the light which impinges on it and which is emitted from the light source 7. The photons of the light excite certain molecules present in the dialysis liquid such that the emission of fluorescence light may be induced in the sample. The presence, wavelength and intensity of the fluorescence light is detected by means of a detector in form of a spectrometer 9 in a direction perpendicular to the illumination direction of the light emitted from the light source 7. Any other direction which is other than being co-axial with the illumination direction of the light source 7 could be used for detecting the fluorescence light induced in the selected molecules in the dialysis liquid in the cell 6. A co-axial arrangement of the spectrometer would typically result in a strong distortion by the irradiation light but it may also be possible using filters, reflection gratings or a wavelength dependent beam splitters to divide the detected light emitted from the sample from the illumination light. As the wavelengths of the illumination light and the detected light are different from one another, many devices for dividing the different light beams from one another are known in the art.

The intensity of the emitted fluorescence light and, in a preferred embodiment, a portion or the entire fluorescence spectrum is detected by means of the spectrometer 9. In an alternative when only selected emission wavelengths are of interest, filters or other wavelength selective devices could also be present in place of the spectrometer 9 in order to select specific wavelengths to be analysed as to their intensity.

As, in a preferred embodiment, the detection wavelength is different from each of the irradiation wavelengths, the light emitted from the sample can be detected easily by simply blocking the irradiation light from entering into the detector by means of devices known in the art.

This intensity data of the emitted and detected light is communicated to a control and analysis unit 11. In the control and analysis unit 11 the presence and/or concentration of at least one analyte in the sample present in the cell 6 is determined on the basis of the information as to the irradiation wavelength and irradiation intensity, as well as the intensity and wavelength of the detected fluorescence light detected by the spectrometer 9. Each fluorescent molecule has a specific fingerprint as to its fluorescent light spectrum for a specific irradiation wavelength.

This determination can be carried out in different ways, one of which is described further below.

In the apparatus shown in FIG. 1, furthermore, a photo detector 8 is present which is located in a co-axial manner with the irradiation light beam emitted from the light source 7. The photo detector 8 is situated on an opposite side of the light source 7 with the cell 6 in-between and consequently receives the irradiation light of the light source 7 which has passed through the cell 6. In other words, the photo detector 8 is intended to detect the light intensity of the light which has been transmitted through the cell 6 and, thus, which has been partly absorbed and is, thus, attenuated by the sample present in the cell 6. The intensity of light received by the photo detector 8 is also communicated to the control and analysis unit 11.

In order to be in a position to carry out a calibration of the relationship of the light source 7 and the photo detector 8, as well as a calibration of the spectrometer 9, a bypass valve 10 is present, which can be controlled by means of the control and analysis unit 11. By opening the bypass valve 10, fresh dialysis liquid can be delivered to the cell 6 such that only fresh dialysis liquid is present in the cell 6. As soon as the bypass valve 10 is shut again, the dialysis liquid circulates through the filter 3 and the cell 6 receives used dialysis liquid again.

The control and analysis unit 11 may determine the presence and/or concentration of a specific analyte, for example human albumin, in the dialysis liquid on the basis of the fluorescence light received by the spectrometer 9. This can be done, for example, by comparing the fluorescence spectrum measured by the spectrometer 9 with a fluorescence spectrum of a specific molecule—a so called fluorescence fingerprint—which may be stored in a storage 12 in FIG. 1. By comparing the measured fluorescence spectrum with a finger print of a specific molecule, the presence of a specific analyte can be determined.

In order to be in a position to determine the concentration of the analyte, the actual intensity of the spectrum is also of relevance.

Even though in the present description of the preferred embodiments the focus is on the analysis of fluorescence light as the detected light, analyzing other forms of light emission of an excited sample are also contemplated, such as the analysis of Raman scattered light for the determination of the presence and/or concentration of at least one analyte in the used dialysis fluid. The principles of this determination are comparable to the principles outlined above with respect to the analysis of the fluorescence light.

Figure 3:
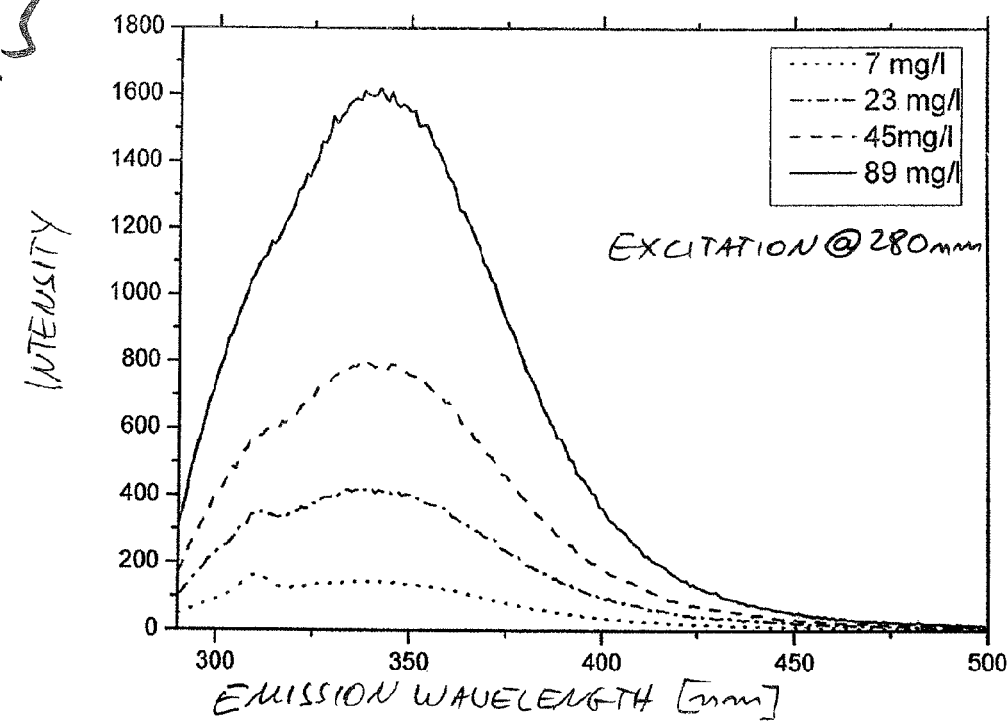
FIG. 3 is a schematic diagram showing the fluorescence spectrum of human albumin in different concentrations after excitation at an irradiation wavelength at 280 nm.

In this respect, FIG. 3 shows the fluorescence spectra for human albumin of different concentrations when being excited with light of a wavelength of 280 nm. Four different concentrations of the human albumin are measured in FIG. 3, namely concentrations of 7 mg/l, 23 mg/l, 45 mg/l and 98 mg/l. It is immediately apparent from FIG. 3 that the maximum fluorescence peak is at approximately 340 nm but that the intensities vary according to the respective concentrations.

Figure 4:
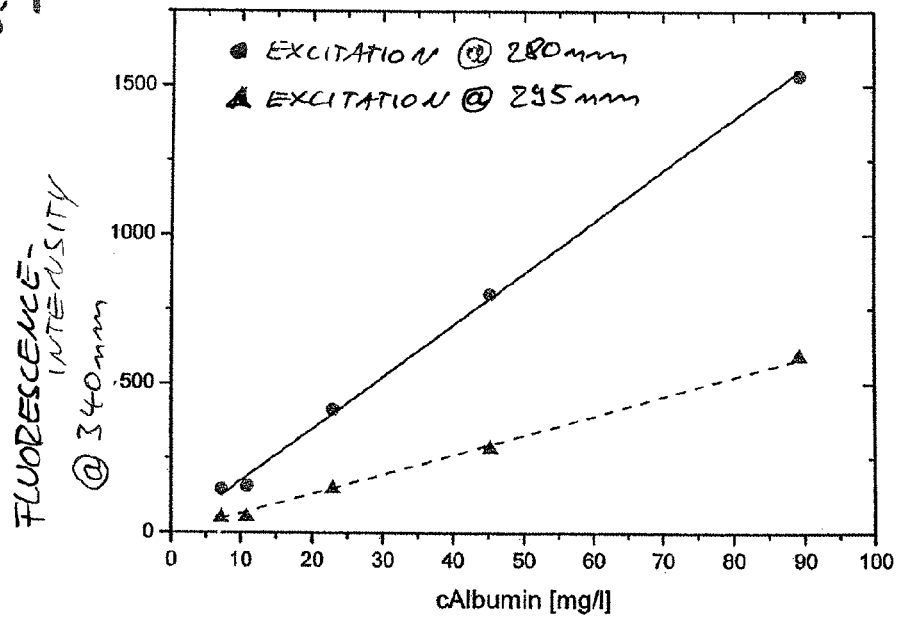
FIG. 4 is a schematic diagram showing the fluorescence intensity of albumin at a detected light wavelength of 340 nm at two different irradiation wavelengths, namely at 280 nm and at 295 nm.

FIG. 4 shows the fluorescence intensity at 340 nm for human albumin at two different excitation wavelengths, namely at 280 nm and at 295 nm.

It is contemplated in the apparatus of FIG. 1 to excite the sample present in the cell 6 at more than one wavelength, for example at two different wavelengths, in order to even more precisely be in a position to determine the presence of a specific molecule, for example human albumin, and also be in a position to determine the actual concentration of this molecule in the dialysis liquid present in the cell 6.

When considering the mechanism of dialysis, it becomes also apparent that it is not only the albumin that will be present in the dialysis liquid in the conduit 5 after it has been passed along the semi-permeable membrane 3, but many other waste products will be present in the dialysis liquid. One is, for example, uric acid.

Figure 5:
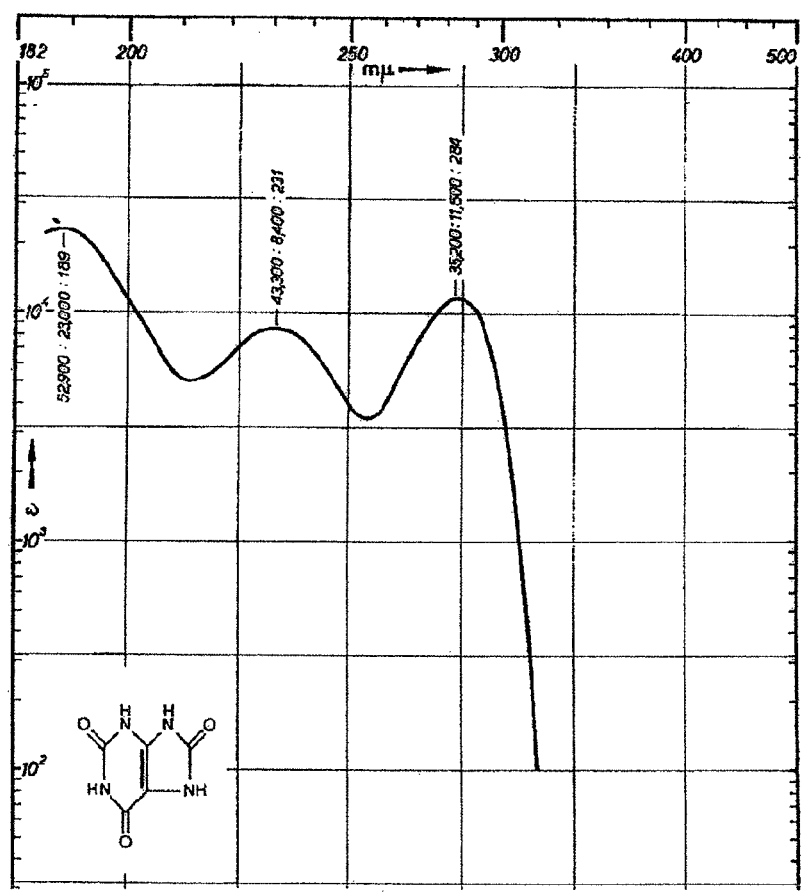
FIG. 5 is a schematic diagram showing the absorption spectrum of uric acid.

Uric acid, however, has a specific absorption spectrum which is shown, schematically, in FIG. 5. FIG. 5 is taken from "*Photoelectric Spectrometry Group, London; Institut für Spektrochemie and Angewandte Spektroskopie, Dortmund* (1968): *DMS UV Atlas of Organic Compounds*. 5 *Volumes. Weinheim, London: Verlag Chemie; Butterworths*".

When considering FIG. 5, it becomes apparent that one absorption peak of uric acid is at about 280 nm which corresponds to the excitation wavelength used for measuring the fluorescence intensity of the human albumin shown in FIG. 3. Accordingly, the higher the concentration of uric acid in the dialysis liquid, the higher is the absorption of the irradiation light. When the excitation wavelength is set at 280 nm, the intensity which is actually applied to a certain volume of the dialysis liquid in the cell 6 is strongly attenuated by means of the presence of the uric acid in the dialysis liquid. Uric acid, however, does not emit any fluorescent light. However, in order to be in a position to reliably determine the intensity of the emitted fluorescent light on the basis of the light intensity emitted by the light source 7, the actual attenuation must be determined.

Figure 2:
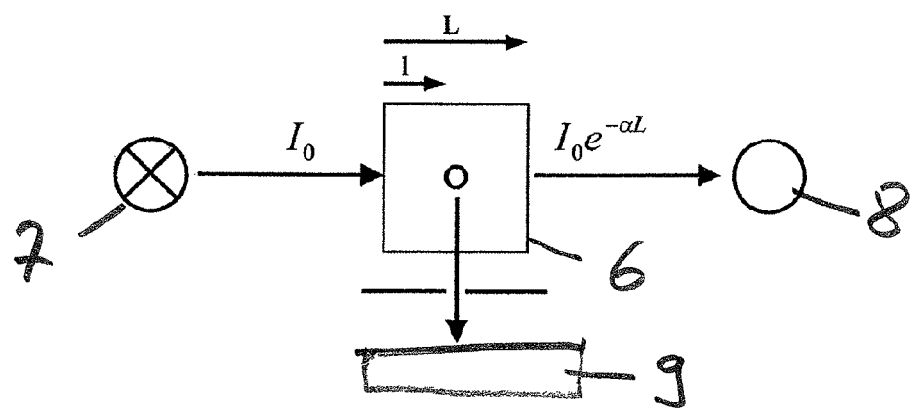
FIG. 2 is a schematic detailed view of a portion of the apparatus according to FIG. 1.

FIG. 2 shows an arrangement for compensating for the absorption of the excitation light in the sample present in the cell 6. The intensity of the light source 7 can be easily determined by measuring the light intensity in the cell 6. However, as the concentration of uric acid in the dialysis liquid varies widely during a dialysis session, it needs to be compensated for.

Accordingly, the intensity of the light at the excitation volume can be calculated on the basis of the Lambert-Beer law, dealing with the absorption of light in material through which the light is traveling:

$$I(x) = I_0 e^{-\alpha x}$$

Here, $I_0$ is the initial intensity of the light impinging on the cell, $I(x)$ is the intensity after the light has been travelled by a distance x through the cell 6 and the coefficient $\alpha$ is a measure for the absorption strength.

Accordingly, after the light has passed through the entire cell 6 of the length L, the intensity is:

$$I(L) = I_0 e^{-\alpha L}$$

Accordingly, assuming that the sample from which the fluorescence light is emitted is distanced by the distance l from the light entrance into the cell, the intensity in the sample is:

$$I(l) = I_0 e^{-\alpha l}$$

The photo detector 8 continuously measures the intensity $I(L)$, namely the intensity of the light that has travelled through the entire cell 6. Provided the initial intensity $I_0$ of the light source 7 remains constant, the coefficient $\alpha$ may be determined such that the light intensity $I(l)$ in the sample which emits the fluorescence light can be calculated at any time. Accordingly, all fluorescence spectra or fluorescence light can be compensated for the absorption in the dialysis liquid present in the cell 6. In other words, the concentration of the respective analyte can be determined because the intensity $I(l)$ of the irradiation light in the sample is known.

In an alternative or in addition to the measurement of the absorption, the excitation intensity of the light emitted by the light source 7 can be determined by analyzing the Raman scattering on water molecules present in the sample in the cell 6. To this end, preferably a Raman spectrum of the sample is obtained. In an alternative, it may be sufficient if only the intensity of the Raman scattered light peak on water for the respective irradiation light is measured. In other words, it is sufficient to measure the Raman peak of water for the respective irradiation light in order to determine the damping of the irradiation light in water.

The intensity of the Raman scattering is substantially proportional to the intensity of the excitation light and of the density of the water molecules in the sample. The density of the water molecules in the sample is, however, substantially constant in the dialysis liquid. Accordingly, by obtaining the Raman spectrum of the sample which also emits the fluorescence light it becomes possible determining the excitation intensity present in the sample. The Raman spectrum may be obtained using the spectrometer 9 as well.

The spectrometer 9 used may be a conventional spectrometer which is readily available on the market. Such a spectrometer typically comprises an input lens for focusing the incident light, a diffraction grating and a (line) CCD-camera for detecting the light.

Fluorescence spectra in a real dialysis liquid are, however, typically not emitted by a single fluorescent molecule only but usually comprise at least two spectra which are superposed. At least the molecules of albumin and indoxyl sulfate must be considered here.

For the purpose of a reliable monitoring of a treatment of a patient it is, however, desirable to know about the presence and/or concentration of more than one analytes in the used dialysis liquid. For example, the medical practitioner is interested in whether human albumin and/or indoxyl sulfate are present in the used dialysis liquid and if any of these analytes is present, the medical practitioner likes to know the concentration thereof.

For the following analysis it is assumed that the fluorescence spectrum which is emitted from the sample after excitation at a specific irradiation wavelength is actually measured by means of the spectrometer 9. The fluorescence spectrum is signified as f(λ) and is considered to be represented by linear superposition of the different fluorescence spectra of N single fluorophores:

$$f(\lambda) = \sum_{i=1}^{N} c_i s_i(\lambda)$$

In this equation, $c_i$ is the concentration of the $i^{th}$ fluorophore and $s_i(\lambda)$ is the respective fluorescence sensitivity of the $i^{th}$ fluorophore as a function of the respective emission wavelength λ. If the spectrum is recorded at M different wavelengths $\lambda_j$, the above equation can be given as a system of M equations with N unknowns:

$$\begin{pmatrix} f(\lambda_1) \\ f(\lambda_2) \\ \vdots \\ f(\lambda_M) \end{pmatrix} = \begin{pmatrix} s_1(\lambda_1) & s_2(\lambda_1) & \ldots & s_N(\lambda_1) \\ s_1(\lambda_2) & s_2(\lambda_2) & \ldots & s_N(\lambda_2) \\ \vdots & \vdots & \ddots & \vdots \\ s_1(\lambda_M) & s_2(\lambda_M) & \ldots & s_N(\lambda_M) \end{pmatrix} \begin{pmatrix} c_1 \\ c_2 \\ \vdots \\ c_N \end{pmatrix}$$

Accordingly, the unknown concentrations $c_i$ may be calculated from the measured spectral intensities $f(\lambda_j)$ taking into account the known matrix elements $s_i(\lambda_j)$. The matrix elements $s_i(\lambda_j)$ may be considered representing the "fluorescence fingerprint" of the respective analytes.

The above system of equations can be solved, in particular numerically. For example, the best solution for the above system of equations is considered the one, which provides, when being inserted into the above matrix, the (theoretical) superposition spectrum which has the lowest square deviation from the actually measured spectrum. By means of this analysis it becomes possible determining the composition of the dialysis fluid by analyzing the detected fluorescence light and in particular by analyzing the respective spectrum of the detected fluorescence light. In particular, the unknown concentrations $c_i$ are determined and, thus, the composition of the used dialysis fluid with respect to the concentrations $c_i$ of the respective analytes can be determined.

In an alternative, more than one irradiation wavelengths are used in the irradiation light. In particular, P different irradiation wavelengths $\lambda_{irr}$ are used in this method—for example by providing different irradiation light diodes. For each irradiation wavelength $\lambda_{irr}$ the intensities $f(\lambda_{irr},\lambda)$ are recorded for the respective emission wavelengths λ. The thus detected spectrum $f(\lambda_{irr},\lambda)$ for one irradiation wavelength is assumed, again, to be given in the form of a linear superposition of the fluorescence spectra of the N analytes:

$$f(\lambda_{irr}, \lambda) = \sum_{i=1}^{N} c_i s_i(\lambda_{irr}, \lambda)$$

$c_i$ being the unknown concentration of the $i^{th}$ analyte and $s_i(\lambda_{irr},\lambda)$ being the known fluorescence sensitivity of the $i^{th}$ analyte as a function of the fluorescence wavelength λ at the respective irradiation wavelength $\lambda_{irr}$.

By adding the respective equations to the linear equation system given above, it reads:

$$\begin{pmatrix} f(\lambda_{irr1}, \lambda_1) \\ f(\lambda_{irr1}, \lambda_2) \\ \vdots \\ f(\lambda_{irr1}, \lambda_M) \\ f(\lambda_{irr2}, \lambda_1) \\ f(\lambda_{irr2}, \lambda_2) \\ \vdots \\ f(\lambda_{irr2}, \lambda_M) \\ \vdots \\ f(\lambda_{irrP}, \lambda_1) \\ \vdots \\ f(\lambda_{irrP}, \lambda_M) \end{pmatrix} = \begin{pmatrix} s_1(\lambda_{irr1}, \lambda_1) & s_2(\lambda_{irr1}, \lambda_1) & \ldots & s_N(\lambda_{irr1}, \lambda_1) \\ s_1(\lambda_{irr1}, \lambda_2) & s_2(\lambda_{irr1}, \lambda_2) & \ldots & s_N(\lambda_{irr1}, \lambda_2) \\ \vdots & \vdots & \ldots & \vdots \\ s_1(\lambda_{irr1}, \lambda_M) & s_2(\lambda_{irr1}, \lambda_M) & \ldots & s_N(\lambda_{irr1}, \lambda_M) \\ s_1(\lambda_{irr2}, \lambda_1) & s_2(\lambda_{irr2}, \lambda_1) & \ldots & s_N(\lambda_{irr2}, \lambda_1) \\ s_1(\lambda_{irr2}, \lambda_2) & s_2(\lambda_{irr2}, \lambda_2) & \ldots & s_N(\lambda_{irr2}, \lambda_2) \\ \vdots & \vdots & \ldots & \vdots \\ s_1(\lambda_{irr2}, \lambda_M) & s_2(\lambda_{irr2}, \lambda_M) & \ldots & s_N(\lambda_{irr2}, \lambda_M) \\ \vdots & \vdots & \ldots & \vdots \\ s_1(\lambda_{irrP}, \lambda_1) & s_2(\lambda_{irr}, \lambda_1) & \ldots & s_N(\lambda_{irrP}, \lambda_1) \\ \vdots & \vdots & \ldots & \vdots \\ s_1(\lambda_{irrP}, \lambda_M) & s_2(\lambda_{irrP}, \lambda_M) & \ldots & s_N(\lambda_{irrP}, \lambda_M) \end{pmatrix} \begin{pmatrix} c_1 \\ c_2 \\ \vdots \\ \vdots \\ \vdots \\ \vdots \\ \vdots \\ \vdots \\ \vdots \\ \vdots \\ \vdots \\ c_N \end{pmatrix}$$

By solving the above equation system, preferably in the same fashion as indicated above, a solution for the concentrations $c_i$ can be determined and, thus, the concentrations of the respective analytes in the used dialysis liquid can be determined.

In further preferred embodiments, the fluorescence spectra are measured by means of the spectrometer 9 in a time resolved manner. In order to accomplish this, the excitation light emitted from the light source 7 is preferably provided in a non-continuous manner, for example in a pulsed manner. For example, a pulsed laser may be used for probing the sample. By means of the provision of time-resolved fluorescence spectra, further information as to the presence and/or concentration of certain analytes can be derived from the sample.

In order to separate several fluorophores in a dialysis liquid, it is also possible, besides the numerical analysis of the fluorescence spectrum as outlined above, using techniques to separate the sample into different fractions. This fractioning can be done, for example, by ultrafiltration of proteins which can be separated due to their high mass number from lower mass substances such as indoxyl sulfate. To achieve filtration, the dialysis solution which is going to be analyzed is fed through a filter with a suitable pore size. The filtrate and/or the concentrate can then be analyzed by irradiating it with light of the at least first wavelength and detecting the fluorescence light emitted by the respective fraction.

For the analysis of the dialysis liquid in the sample, it is contemplated analyzing it either in a separate branch of the dialysis apparatus, or by storing it in a separate volume, where it is treated and then feeding it again through the measurement cell 6.

Figure 6:
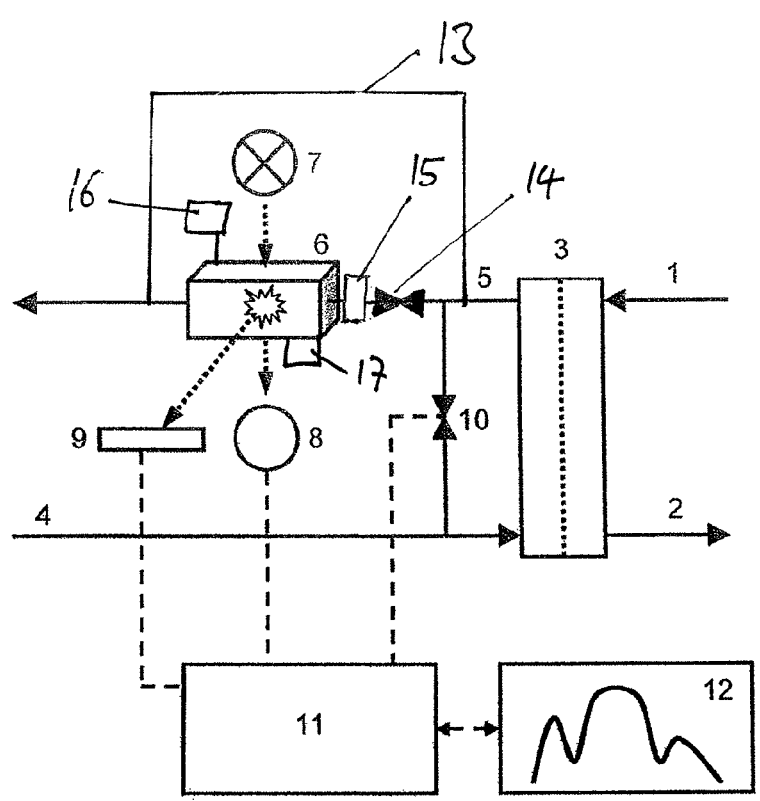
FIG. 6 is a schematic layout of an apparatus for carrying out an analysis on used dialysis fluid.

FIG. 6 shows schematically a layout of an apparatus which is arranged for carrying out the analysis on the used dialysis fluid separated from the main flow of the used dialysis fluid. To this end, a bypass conduit 13 is shown through which the larger portion of the used dialysis fluid passes. Accordingly, only a fraction of the flow of the used dialysis fluid output after having passed the membrane 3 flows through the cell 6.

Preferably, a valve 14 is present before the cell 6 such that samples can be separated from the constant flow of the used analyte. The separated flows can be analysed over a sufficiently long time such that also time resolved analysis on the identical sample can be carried out before it is discharged again. By means of the valve 14 it is also possible switching between a constant flow mode in the cell 6 when the valve 14 is always open, or a separated sample mode when the valve 14 is only opened to let some used dialysis fluid flow into the cell 6 and than close the valve as long as the respective sample is analysed in the cell 6.

A separation of different fractions of the sample can also be achieved in or before the cell 6 by means of electrophoresis, chromatography, filtering cascades, by using specific adsorbers or by marking specific substances or molecules by means of fluorescence active markers. A respective apparatus for carrying out the respective treatments on the sample before it is analysed in the cell 6 is schematically shown at reference numeral 15.

In a further preferred embodiment, the sample may be measured at least twice wherein the second measurement is carried out after the sample is physically and/or chemically treated. The actual treatment may be carried out by heating, by adding and/or removing reagents such as an acid, a chemical base or a salt, or by any other suitable treatment. The presence and/or concentration of a specific analyte is then determined taking into account the difference between the at least two measurements, namely the measurement before the treatment and the measurement after the treatment. The combination of the difference of the two fluorescence spectra and the fluorescence spectrum as such may provide additional information as to the respective analyte—or the composition of different analytes—in the dialysis liquid.

The respective apparatus for treating the sample is shown schematically in FIG. 6 at reference numeral 16, which may be a dosing apparatus for adding chemicals to the sample, and at reference numeral 17, which is an apparatus for physical treatment such as a heater.

As to the light source 7, it is also contemplated using, in a preferred embodiment, polarized light for exciting the dialysis liquid, in particular left-handed circularly polarized light and/or right-hand circularly polarized light.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of monitoring a treatment of a patient, the method comprising the steps of:
    irradiating a sample of a liquid used in, the treatment with irradiation light of at least a first irradiation wavelength;
    detecting light emitted by the irradiated sample in at least a first detection wavelength, the detection wavelength being different from the first irradiation wavelength; and
    determining the presence and/or concentration of at least one analyte in the sample based on the detected light,
    the liquid being a dialysis liquid and the detected light including fluorescence light, and the presence and/or concentration of the at least one analyte in the sample being determined based on the detected fluorescence light, with the irradiation light being a UV-light having a wavelength of between 180 nm and 400 nm.

2. The method according to claim 1,
    wherein the presence and/or concentration of the analyte in the sample is determined based on the detected light of at least a first detection wavelength and a second detection wavelength, the first and second detection wavelengths being different from one another, and/or
    wherein the presence and/or concentration of the analyte in the sample is determined based on the spectrum of the detected light of the sample.

3. The method according to claim 1,
    wherein the irradiation light is UV-light having a wavelength between 250 nm and 300 nm, or having a wavelength of 280 nm and/or 295 nm, and/or
    wherein the sample is irradiated with irradiation light of at least two separated, distinct wavelengths.

4. The method of claim 3, wherein the irradiation light has a wavelength of 280 cm and of 295 nm.

5. The method according to claim 1,
    wherein the intensity of the irradiation light in the sample is determined and the determination of the presence and/or concentration of the analyte in the sample is compensated for the intensity of the irradiation light,
    wherein the absorption of the irradiation light in the sample is measured and the intensity of the irradiation light is determined on the basis of the measured absorption,
    wherein the absorption in the sample is measured by a photo detector detecting the irradiation light transmitted through the sample and/or wherein Raman scattered light of the sample is obtained and the intensity of the irradiation light in the sample is determined based on the the obtained Raman scattered light, and/or
    wherein a Raman spectrum of the sample and/or the intensity at a water Raman peak of the Raman scattered light is obtained.

6. The method according to claim 1, wherein the detected light is detected in a time resolved manner.

7. The method of claim 6, wherein the irradiation light is pulsed.

8. The method according to claim 1, wherein the sample is irradiated with polarized irradiation light.

9. The method of claim 8, wherein the polarized irradiation light is at least one of left-handed circularly polarized irradiation light and right-handed circularly polarized irradiation light.

10. The method according to claim 1,
    wherein the light emitted by the sample is detected at least twice,
    wherein between the first and second detections the sample is treated physically and/or chemically and the presence and/or concentration of the analyte is determined taking into account the difference between the first and second detections, and
    wherein the sample is treated by heating, by adding and/or removing of reagents and/or by adding and/or removing of an acid, of a chemical base and/or of a salt.

11. The method according to claim 1,
    wherein the sample is separated from the flow of dialysis liquid for carrying out the determination of the presence and/or concentration of the analyte, or
    wherein the determination of the presence and/or concentration of the analyte is carried out continuously on the flow of dialysis liquid.

12. The method according to claim 1,
    wherein before irradiating the sample with the irradiation light, the sample is separated into different fractions, and
    wherein at least one of the fractions of the sample is irradiated with the irradiation light.

13. The method of claim 12, wherein the sample is separated into the different fractions by at least one of ultrafiltration, electrophoresis, chromatography, addition of an absorber, and addition of a fluorescent marker.

14. The method according to claim 1,
    wherein the presence and/or concentration of at least two different analytes is determined based on the detected light, wherein after excitation at a specific irradiation wavelength the detected light is analysed for a presence of at least N different analytes by analyzing the detected light $f(\lambda)$ to be given as a linear superposition of the spectra of the N analytes, with ci being an unknown concentration of an ith analyte and $si(\lambda)$ being a known sensitivity of the ith analyte as a function of a respective emission wavelength $\lambda$, and solving for the unknown concentrations ci by determining the spectrum at M different wavelengths $\lambda j$, considering the linear superposition as a system of M equations with N unknowns, and solving the system numerically, by considering as a best solution for the system of equations the solution which provides, when being inserted into the system of equations, a superposition spectrum which has a lowest square deviation from an actually measured spectrum.

15. The method according to claim wherein the method monitors at least one of hemodialysis, hemodiafiltration, and peritoneal dialysis.

16. An apparatus for monitoring a treatment of a patient, the apparatus comprising:
a light source for irradiating a sample of a liquid used in the treatment with irradiation light of at least a first irradiation wavelength;
a detector for detecting light emitted by the irradiated sample in at least a first detection wavelength, the detection wavelength being different from the first irradiation wavelength; and
a control and analysis unit for determining the presence and/or concentration of at least one analyte in the sample based on the detected light,
the liquid being a dialysis liquid and the detector being arranged to detect light including fluorescence light, and the control and analysis unit being arranged to determine the presence and/or concentration of the at least one analyte in the sample based on the detected fluorescence light, with the light source emitting irradiation light in a UV-range having a wavelength of between 180 nm and 400 nm.

17. The apparatus according to claim 16,
wherein the light source emits irradiation light in the UV range between 250 nm and 300 nm, or at 280 nm and/or 295 nm, and/or
wherein the light source AlInGaN diode, and/or
wherein the light source is set to provide illumination light in at least two separated, distinct, wavelengths.

18. The apparatus of claim 17, wherein the irradiation light has a wavelength of 280 nm and of 295 nm.

19. The apparatus according to claim 16, further comprising an element for determining an intensity of the irradiation light in the sample, wherein the device includes a photo detector for determining an absorption of the irradiation light in the sample of dialysis liquid and/or includes an element for obtaining Raman spectrum and/or an intensity of Raman scattered light at at least a specific wavelength.

20. The apparatus according to claim 16, further comprising an element for treating the sample physically and/or chemically and an element for separating the sample into different fractions.

21. The apparatus according to claim 20, wherein the element for treating treats the sample by heating, by adding and/or removing of reagents, and/or by adding and/or removing of an acid, of a chemical base, and/or of a salt.

22. The apparatus according to claim 20, wherein the element for separating separates the sample into the different fractions by at least one of ultrafiltration, electrophoresis, chromatography, addition of an absorber, and addition of a fluorescent marker.

23. The apparatus according to claim 16,
wherein the control and analysis unit is arranged to determine the presence and/or concentration of at least two different analytes based on the detected light,
wherein the control and analysis unit is arranged to analyze the detected light, after excitation at a specific irradiation wavelength, for a presence of at least N different analytes by analyzing the detected light $f(\lambda)$ as a linear superposition of the spectra of the N analytes, with ci being an unknown concentration of an ith analyte and $si(\lambda)$ being a known sensitivity of the ith analyte as a function of a respective emission wavelength $\lambda$,
wherein the control and analysis unit is arranged to solve for the unknown concentrations ci by determining the spectrum at M different wavelengths $\lambda j$, considering the linear superposition as a system of M equations with N unknowns, and by solving the system numerically, by considering as a best solution for the system of equations the solution which provides, when being inserted into the system of equations, a superposition spectrum which has a lowest square deviation from an actually measured spectrum.

24. The apparatus according to claim 16, wherein the apparatus monitors at least one of hemodialysis, hemodiafiltration, and peritoneal dialysis.

* * * * *